United States Patent
Nishigaki

(10) Patent No.: US 6,493,081 B1
(45) Date of Patent: Dec. 10, 2002

(54) FLAME-TYPE ATOMIC ABSORPTION SPECTROPHOTOMETER

(75) Inventor: Hidehisa Nishigaki, Shiga (JP)

(73) Assignee: Shimadzu Corporation, Kyoto (JP)

( * ) Notice: Subject to any disclaimer, the term of this patent is extended or adjusted under 35 U.S.C. 154(b) by 78 days.

(21) Appl. No.: 09/697,063

(22) Filed: Oct. 26, 2000

(30) Foreign Application Priority Data

Mar. 30, 2000 (JP) ........................................ 2000-093389

(51) Int. Cl.⁷ .............................. F23N 3/00; F23N 5/08
(52) U.S. Cl. ......................... 356/315; 356/417; 431/4; 431/14; 431/79; 431/89
(58) Field of Search ................................ 356/315, 417; 431/79, 4, 14, 89

(56) References Cited

U.S. PATENT DOCUMENTS

| | | | |
|---|---|---|---|
| 4,571,172 A | * | 2/1986 | Kendall-Tobias ............ 356/315 |
| 4,640,677 A | * | 2/1987 | Huber ........................ 431/89 |
| 4,653,998 A | * | 3/1987 | Sohma et al. ................ 356/315 |
| 6,244,857 B1 | * | 6/2001 | VonDrasek et al. ............ 431/79 |

* cited by examiner

Primary Examiner—Jack Berman
(74) Attorney, Agent, or Firm—Beyer Weaver & Thomas LLP

(57) ABSTRACT

A flame-type atomic absorption spectrophotometer forms a flame by igniting a mixture of a fuel gas and a first combustion support gas such as air and then the first combustion support gas is replaced by a second combustion support gas such as nitrous oxide with a faster combustion speed. An optical sensor is disposed near the flame to detect the quantity of light therefrom. A gas flow rate control device independently controls the flow rates of the fuel gas, the first combustion support gas and the second combustion support gas to the flame. A combustion control unit serves to switch the gas to be supplied to the flame from the first combustion support gas to the second combustion support gas, based on how much the quantity of light detected by the optical sensor changes between the time of ignition and after the flow rate of the fuel gas and/or the first combustion support gas is changed.

20 Claims, 2 Drawing Sheets

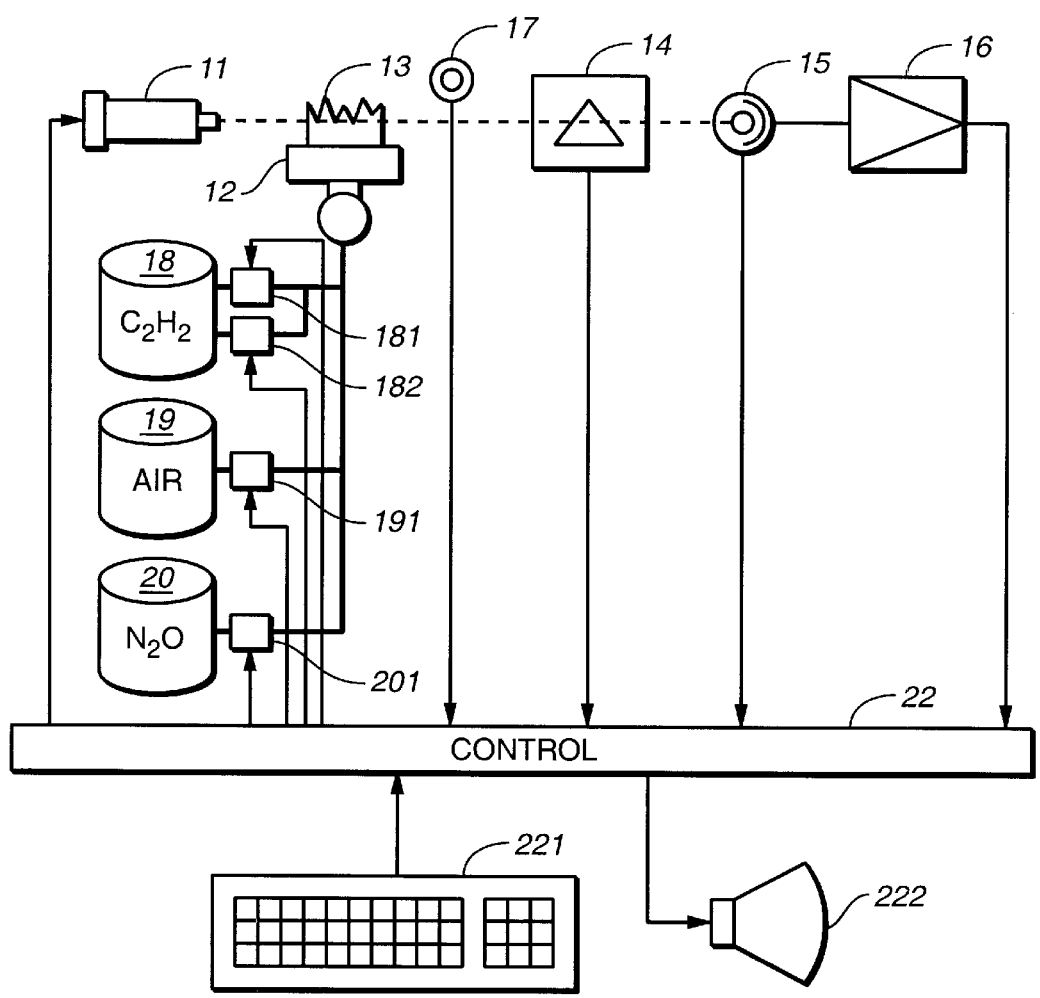
FIG._1

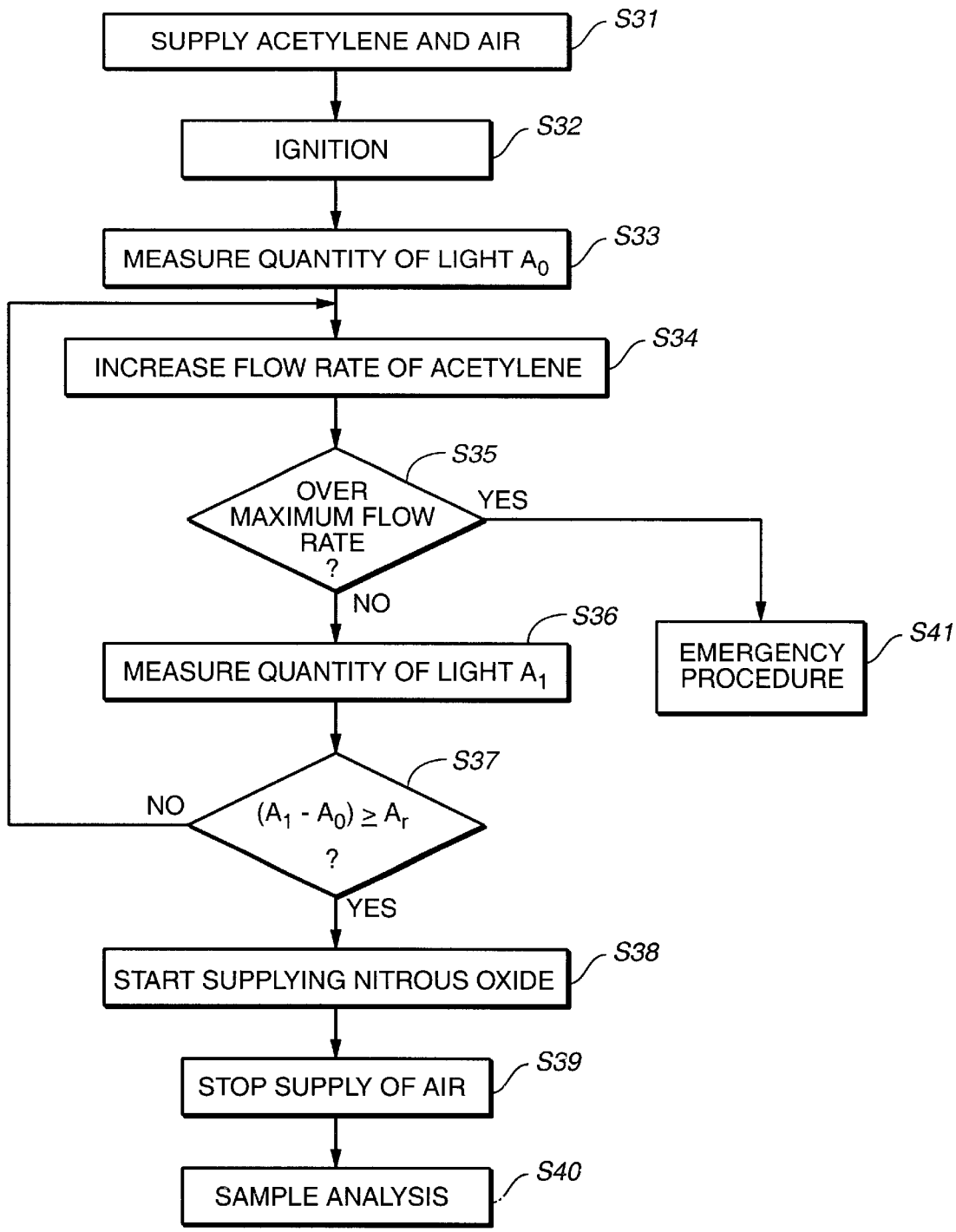
FIG._2

FLAME-TYPE ATOMIC ABSORPTION SPECTROPHOTOMETER

BACKGROUND OF THE INVENTION

This invention relates to a flame-type atomic absorption spectrophotometer adapted to atomize a sample by introducing an atomized sample liquid into a flame.

It is necessary with an atomic absorption spectrophotometer to convert a sample into an atomic vapor. Methods of atomization include the flame method which makes use of a chemical flame and the flameless method which does not use a chemical flame. A flame-type atomic absorption spectrophotometer forms a flame by mixing together inside a chamber a fuel gas and a combustion support gas which are supplied separately. This mixture is then caused to flow out of the slit opening of a burner and to undergo combustion. The kinds of the fuel gas and the combustion support gas, the flow rate of the fuel gas and the height (or the vertical position) of the burner are variously determined, depending on the target element to be analyzed. In other words, these parameters for a flame-type atomic absorption spectrophotometer must be changed appropriately according to the kind of element to be measured. Although acetylene ($C_2H_2$) and air are most frequently used as the fuel gas and the combustion support gas, respectively, nitrous oxide ($N_2O$) is sometimes used as the combustion support gas when an element which forms a strong oxide in the flame such as aluminum and titanium is to be analyzed, because $N_2O$ is capable of forming a flame which is hotter and more strongly reductive.

Since the mixture of nitrous oxide and acetylene has a very high speed of combustion, there may be a backfire if it is directly ignited or the supply of both gases is stopped simultaneously when the flame is extinguished. Thus, for using a flame of nitrous oxide-acetylene gas, it has been known to initially supply a mixture of air and acetylene to the burner to ignite and then to increase the flow rate of the acetylene and thereafter to replace air with nitrous oxide. For effecting this ignition procedure, it has been known (as described in Japanese Patent Publication Tokko 60-22291) to check the increase in the flow rate of acetylene by detecting an increase in the quantity of emitted light from the flame by means of an optical sensor or the like. According to the prior method of carrying out this procedure, it was concluded that the flow rate of acetylene has sufficiently increased when the detected light intensity value has exceeded a predetermined reference value. If the initial flow rate of the air-acetylene mixture is large, and especially if the flow rate of acetylene is large, however, the light intensity is already large during the initial period and it may have exceeded the predetermined reference value. In such a situation, a further increase in the flow rate of acetylene cannot be detected and the switch-over to nitrous oxide cannot be effected.

SUMMARY OF THE INVENTION

It is therefore an object of this invention in view of such a situation to provide an improved flame-type atomic absorption spectrophotometer which, when using nitrous oxide as the combustion support gas, can dependably carry out the switching from an air-acetylene mixture to a nitrous oxide-acetylene mixture at the time of ignition.

A flame-type atomic absorption spectrophotometer embodying this invention, with which the above and other objects can be accomplished, may be characterized as comprising an optical sensor for detecting the quantity of light from its flame, a gas flow rate control device for independently controlling flows of a fuel gas, a first combustion support gas and a second combustion support gas which are supplied to a burner, and a combustion control unit for controlling the gas flow rate control device to stop supplying the first combustion support gas and to start supplying the second combustion support gas instead to the burner for the flame, based on how much the quantity of light detected by the optical sensor changes between the time of ignition and after the flow rate is changed for the fuel gas and/or the first combustion support gas.

The present invention is addressed to such a situation where the flame must be initially formed by usuing a first combustion support gas with a slower combustion speed such as air because the combustion speed of the second combustion support gas such as nitrous oxide is too fast. First, a mixture of the fuel gas and the first combustion support gas is supplied to the burner at a specified rate and ignited. The quantity of light from the flame at this moment is measured and stored in a memory as the initial value.

Prior to switching to the second combustion support gas with a faster combustion speed, the flow rate of the fuel gas is increased. As the flow rate of the fuel gas is increased, the control unit compares the detected quantity of light from the flame with the initial value stored in the memory. If the difference is less than a specified reference value, the control unit keeps increaing the flow rate. As soon as the diffence reaches the reference value, the first combustion support gas is replaced by the second combustion support gas. In this manner, the switching of the combustion support gas can be accomplished without the danger of a backfire.

Depending on the situation, the contol unit may also change the flow rate of the first combustion support gas.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic structural diagram of a flame-type atomic absorption spectrophotometer embodying this invention; and FIG. 2 is a flow chart for the ignition routine for forming a acetylene-nitrous oxide flame for the spectrophotometer of FIG. 1.

DETAILED DESCRIPTION OF THE INVENTION

The invention is described next by way of an example with reference to FIG. 1 wherein numeral 11 indicates a light source for emitting light having a bright line spectrum including the resonance line of the target element to be analyzed and passing through a flame 13 from a burner 12. Although not illustrated in FIG. 1, a sample providing device for providing a sample in the form of small liquid droplets to the flame 13 is provided near the burner 12. As the light from the source 11 passes through the sample atomized by the flame 13, it is absorbed thereby at the wavelength depending on the kind of the sample and in an amount corresponding to the quantity of the sample. The light which has been transmitted is dispersed by a spectroscope 14 and the light with the specific wavelength corresponding to the bright line with the highest absorptivity by the target element (normally the resonance line) is taken out and guided to an optical detector 15 which serves to output a signal corresponding to the quantity of light which has been made incident to a signal processor 16. A control unit 22 for controlling the entire apparatus serves to calculate the absorbance at this specified wavelength on the basis of the received detection signal and to carry out a quantitative analysis by performing specified calculations. The user inputs commands to the control unit 22 through an input device 221 to display the result of the analysis on a display device 222.

Connected to the burner 12 for forming the flame 13 are a pressured acetylene container 18 filled with acetylene gas serving as the fuel gas, a pressured air container 19 filled with air serving as the first combustion support gas, and a pressured nitrous oxide container 20 filled with nitrous oxide serving as the second combustion support gas. Two electromagnetic valves (that is, a first valve 181 for initial supply and a second valve 182 for increasing the supply) are connected in parallel to the acetylene container 18 while the air container 19 and the nitrous oxide container 20 are each connected to one electromagnetic valve 191 or 201. Numeral 17 in FIG. 1 indicates an optical sensor disposed near the burner 12 for measuring the quantity of light emitted from the flame 13.

FIG. 2 shows the routine followed by the control unit 22 in controlling the ignition when nitrous oxide is used as the combustion support gas. First, the valves 181 and 182 are opened to specified degrees to supply acetylene and air at a specified ratio to the burner 12 (Step S31) and the mixed gas is ignited (Step S32). After the flame 13 has become stable, the quantity of light $A_0$ from the flame 13 is measured (Step S33) and is stored in a memory.

Next, the valve 182 is opened to a specified initial degree to increase the supply of acetylene (Step S34). As a result, the flame 13 becomes larger and the quantity of emitted light increases. The increased quantity of light ($A_1$) is measured (Step S36) and the control unit 22 calculates its difference from the initial quantity $A_0$ stored in the memory and determines whether this difference $A_1-A_0$ is greater than a predetermined reference value $A_r$ or not (Step S37). If the difference $A_1-A_0$ has not reached the reference value $A_r$ (NO in Step S 37), the program returns to Step S34 and the supply of acetylene gas is further increased.

When the difference $A_1-A_0$ reaches the reference value $A_r$ (YES in Step S37), the valve 201 is opened to a specified degree (Step S38) and the valve 191 is closed (Step S39). A flame of nitrous oxide and acetylene can thus be formed safely without causing any backfire. A sample is thereafter placed inside this flame 13 to carry out an analysis (Step S40).

While the acetylene supply rate is increased with the processes from Step S34 to Step S37 being repeated, the flow rate of acetylene to the burner 12 is monitored to determine whether or not it is above a predetermined maximum value (Step S35). If the acetylene flow rate is found to have reached or exceeded this maximum value (YES in Step S35), although the difference in quantity of light $A_1-A_0$ has not reached the reference value $A_r$, an alarm is outputted and/or other emergency procedures are carried out such as stopping the supply of the fuel gas and the combustion support gas to the burner 12 (Step 41).

In summary, a flame-type atomic absorption spectrophotometer of this invention is different from prior art spectrophotometers in that the switching from the first combustion support gas to the second combustion support gas is carried out on the basis of the difference in the quantity of light between the initial condition when the first combustion support gas is used and after the flow rate of the fuel gas and/or the first combustion support gas has been increased. Thus, even if the initial flow rate of the fuel gas and/or the first combustion support gas is large and hence the initial light quantity from the flame is large, the increase in the flow rate of the fuel gas and/or the first combustion support gas can be ascertained in a dependable fashion.

In situations where the quantity of light from the flame is not increasing according to the increase in the flow rate of the fuel gas and/or the first combustion support gas, it can be readily noted with a warning that something abnormal has happened and an adequate measure can be taken automatically.

What is claimed is:

1. A flame-type atomic absorption spectrophotometer which forms a flame by ignition of a mixture of a fuel gas and a first combustion support gas before forming a flame from another mixture of said fuel gas and a second combustion support gas, said spectrophotometer comprising:

detecting means for detecting quantity of light from said flame;

gas control means for independently controlling flow rates of said fuel gas, said first combustion support gas and said second combustion support gas which are supplied to a burner; and combustion control means for causing said gas control means to stop supplying said first combustion support gas and to start supplying said second combustion support gas to said burner based on the difference in quantity of light detected by said detecting means between at time of said ignition and after a change is made in gas flow rate to said burner.

2. The spectrophotometer of claim 1 wherein said change is in flow rate of said fuel gas.

3. The spectrophotometer of claim 1 wherein said change is in flow rate of said first combustion support gas.

4. The spectrophotometer of claim 1 wherein said change is in flow rate of said fuel gas and said first combustion support gas.

5. The spectrophotometer of claim 1 wherein said second combustion support gas is nitrous oxide.

6. The spectrophotometer of claim 2 wherein said second combustion support gas is nitrous oxide.

7. The spectrophotometer of claim 3 wherein said second combustion support gas is nitrous oxide.

8. The spectrophotometer of claim 4 wherein said second combustion support gas is nitrous oxide.

9. The spectrophotometer of claim 1 wherein said combustion control means further serves to calculate a difference value between quantity of light measured by said detecting means and a predetermined initial light quantity value, to compare said difference value with a specified reference value, to continue increasing supply rate of said fuel gas to said flame after said ignition if said difference value is smaller than said reference value and to stop suppling said first combustion support gas to said flame and to start supply said second combustion support gas to said flame if said difference value has reached said reference value.

10. The spectrophotometer of claim 2 wherein said combustion control means further serves to calculate a difference value between quantity of light measured by said detecting means and a predetermined initial light quantity value, to compare said difference value with a specified reference value, to continue increasing supply rate of said fuel gas to said flame after said ignition if said difference value is smaller than said reference value and to stop suppling said first combustion support gas to said flame and to start supply said second combustion support gas to said flame if said difference value has reached said reference value.

11. The spectrophotometer of claim 3 wherein said combustion control means further serves to calculate a difference value between quantity of light measured by said detecting means and a predetermined initial light quantity value, to compare said difference value with a specified reference value, to continue increasing supply rate of said fuel gas to said flame after said ignition if said difference value is smaller than said reference value and to stop suppling said first combustion support gas to said flame and to start supply said second combustion support gas to said flame if said difference value has reached said reference value.

12. The spectrophotometer of claim 4 wherein said combustion control means further serves to calculate a difference value between quantity of light measured by said detecting means and a predetermined initial light quantity value, to compare said difference value with a specified reference value, to continue increasing supply rate of said fuel gas to said flame after said ignition if said difference value is smaller than said reference value and to stop suppling said first combustion support gas to said flame and to start supply said second combustion support gas to said flame if said difference value has reached said reference value.

13. The spectrophotometer of claim 9 wherein said combustion control means further serves to carry out emergency procedures if flow rate of said fuel gas, while being increased, exceeds a predetermined maximum value regardless of whether said difference value is larger or smaller than said reference value.

14. The spectrophotometer of claim 10 wherein said combustion control means further serves to carry out emergency procedures if flow rate of said fuel gas, while being increased, exceeds a predetermined maximum value regardless of whether said difference value is larger or smaller than said reference value.

15. The spectrophotometer of claim 11 wherein said combustion control means further serves to carry out emergency procedures if flow rate of said fuel gas, while being increased, exceeds a predetermined maximum value regardless of whether said difference value is larger or smaller than said reference value.

16. The spectrophotometer of claim 12 wherein said combustion control means further serves to carry out emergency procedures if flow rate of said fuel gas, while being increased, exceeds a predetermined maximum value regardless of whether said difference value is larger or smaller than said reference value.

17. The spectrophotometer of claim 1 wherein said gas control means include containers for said fuel gas, said first combustion support gas and said second combustion support gas, a valve for initial supply of said fuel gas, another valve for additionally supplying said fuel gas, a third valve for supply said first combustion support gas and a fourth valve for supplying said second combustion support gas.

18. The spectrophotometer of claim 2 wherein said gas control means include containers for said fuel gas, said first combustion support gas and said second combustion support gas, a valve for initial supply of said fuel gas, another valve for additionally supplying said fuel gas, a third valve for supply said first combustion support gas and a fourth valve for supplying said second combustion support gas.

19. The spectrophotometer of claim 3 wherein said gas control means include containers for said fuel gas, said first combustion support gas and said second combustion support gas, a valve for initial supply of said fuel gas, another valve for additionally supplying said fuel gas, a third valve for supply said first combustion support gas and a fourth valve for supplying said second combustion support gas.

20. The spectrophotometer of claim 4 wherein said gas control means include containers for said fuel gas, said first combustion support gas and said second combustion support gas, a valve for initial supply of said fuel gas, another valve for additionally supplying said fuel gas, a third valve for supply said first combustion support gas and a fourth valve for supplying said second combustion support gas.

* * * * *